United States Patent [19]
Schricker

[11] Patent Number: 5,817,936
[45] Date of Patent: Oct. 6, 1998

[54] METHOD FOR DETECTING AN ABNORMAL CONDITION OF A ROAD SURFACE BY TRENDING A RESISTANCE FACTOR

[75] Inventor: David R. Schricker, Dunlap, Ill.

[73] Assignee: Caterpillar Inc., Peoria, Ill.

[21] Appl. No.: 811,480

[22] Filed: Mar. 5, 1997

Related U.S. Application Data

[63] Continuation-in-part of Ser. No. 616,869, Mar. 15, 1996, abandoned.

[51] Int. Cl.[6] ............................................. E01C 23/01
[52] U.S. Cl. ................................... 73/146; 73/105
[58] Field of Search ............................. 73/146, 105

[56] References Cited

U.S. PATENT DOCUMENTS 4,837,727  6/1989  Tashiro et al. ..................... 73/105 X
5,635,623  6/1997  Simon ................................. 73/146 X

*Primary Examiner*—Joseph L. Felber
*Attorney, Agent, or Firm*—David M. Masterson; James R. Yee

[57] ABSTRACT

A method for detects a change in the condition of a road traversed by a fleet of at least one mobile machine. The method includes the steps of sensing a plurality of machine parameters as the mobile machine traverses a segment of the road and responsively calculating a plurality of machine resistance factors each time the mobile machine traverses the segment. An average resistance factor is calculated as a function of the series of machine resistance factors and the fleet factor average is trended over time in order to detect a change in the road condition.

11 Claims, 5 Drawing Sheets

Fig-1-
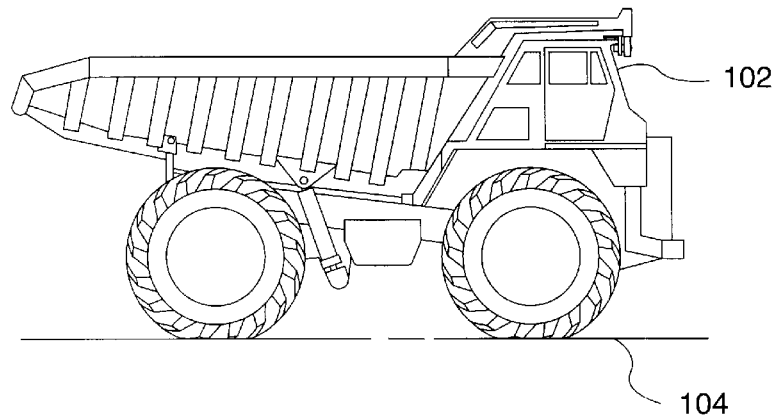
Fig-2-
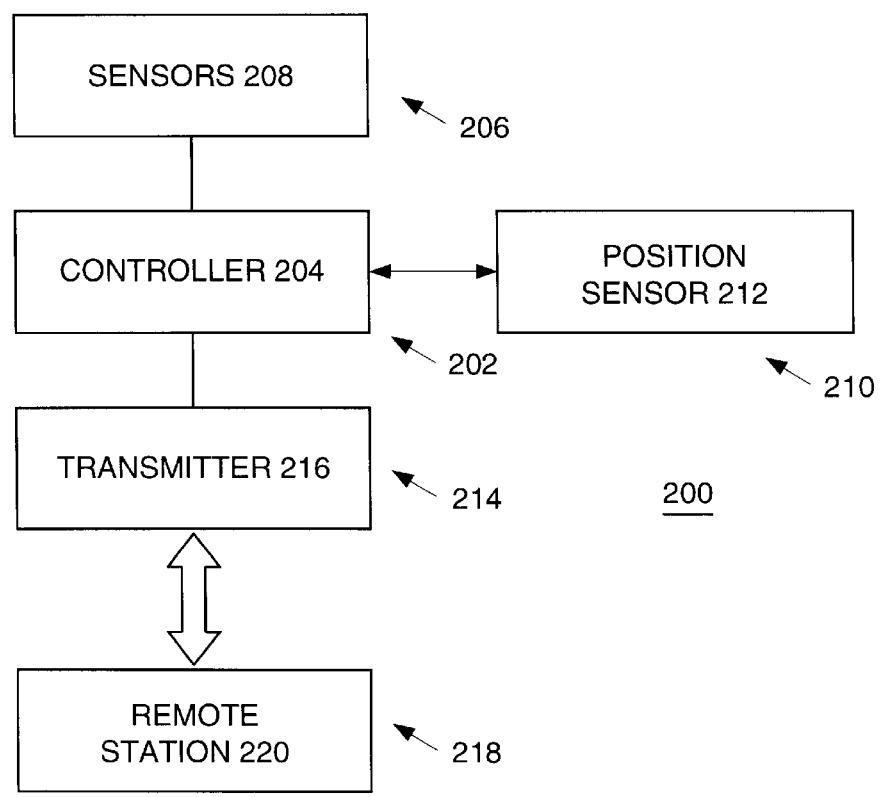

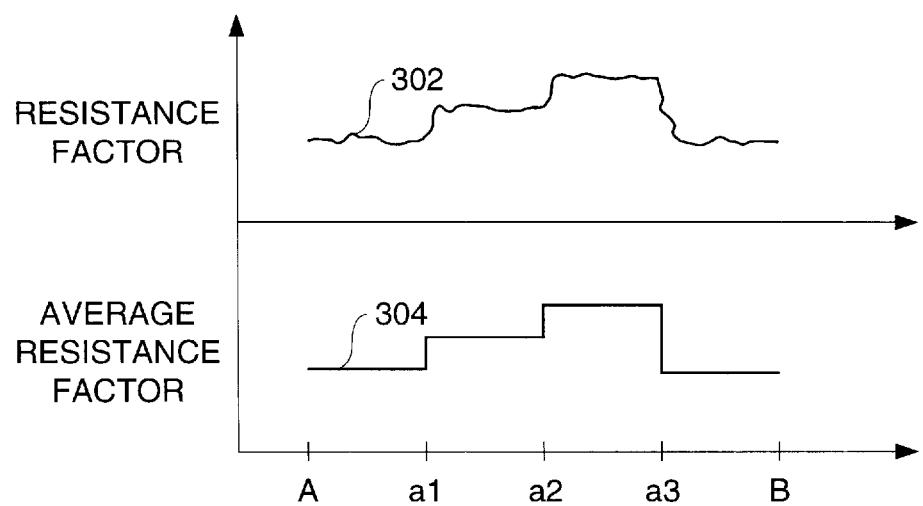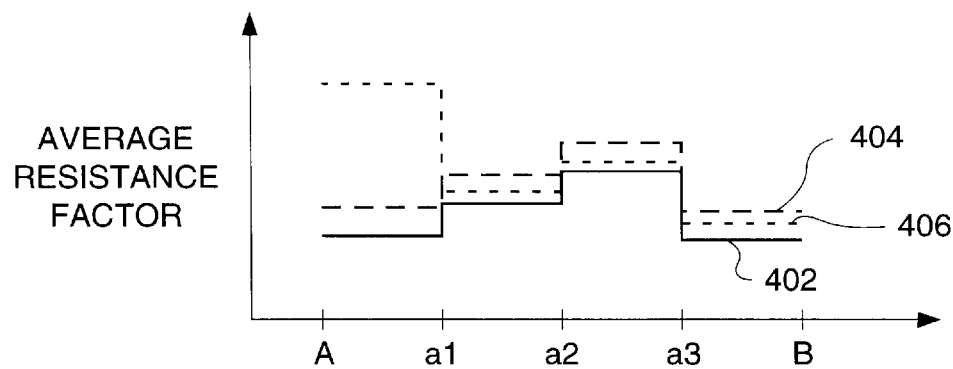

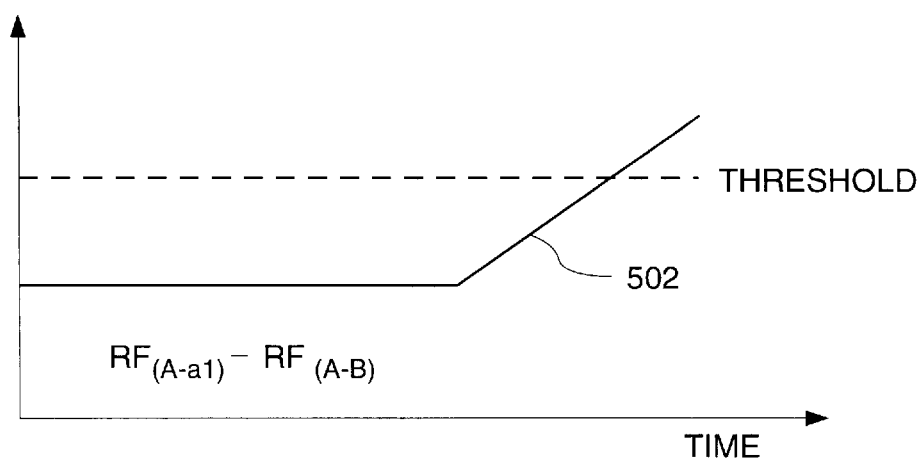
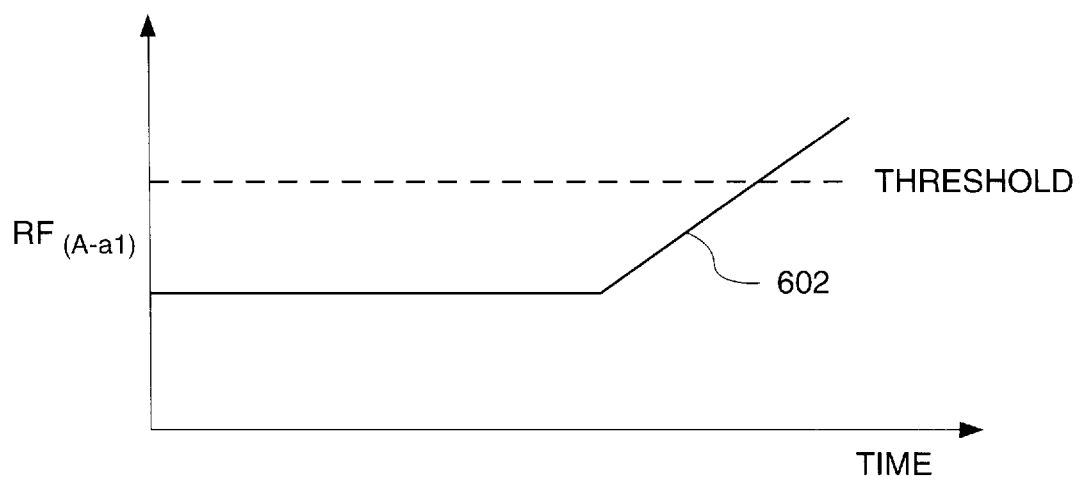

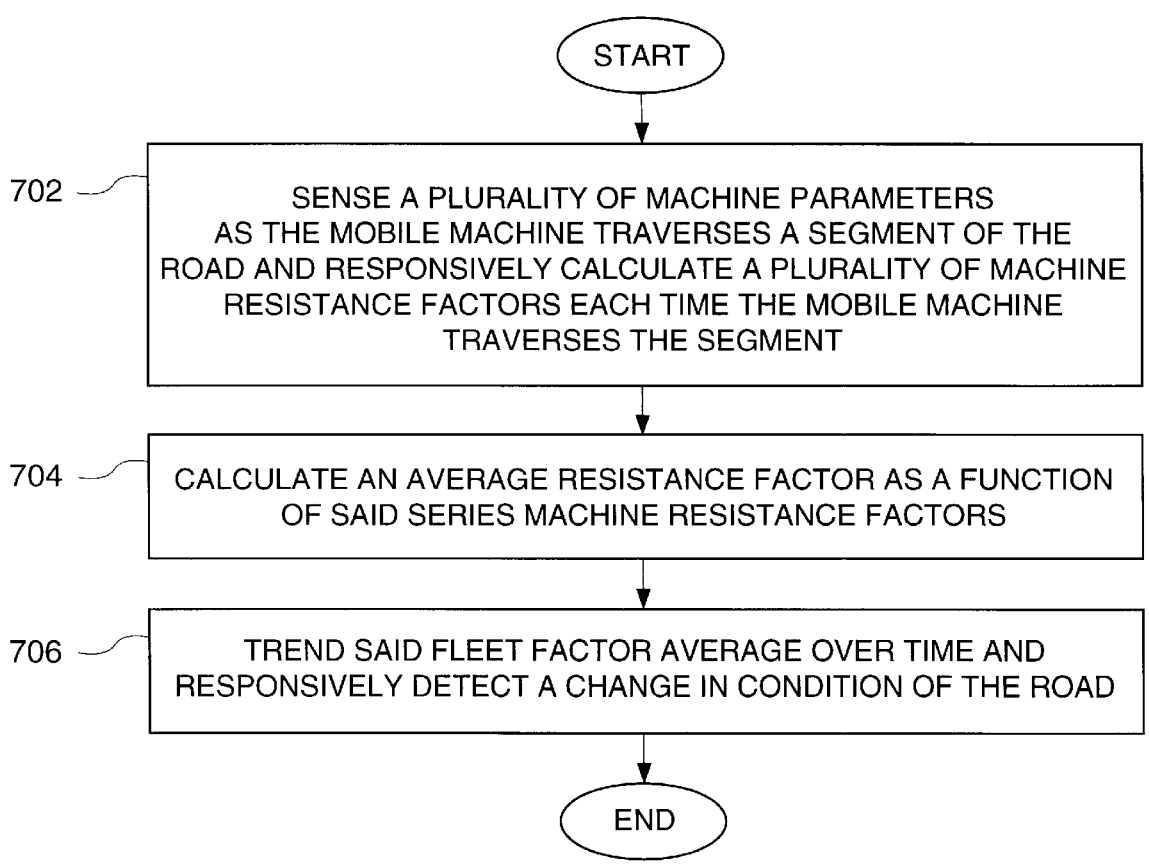

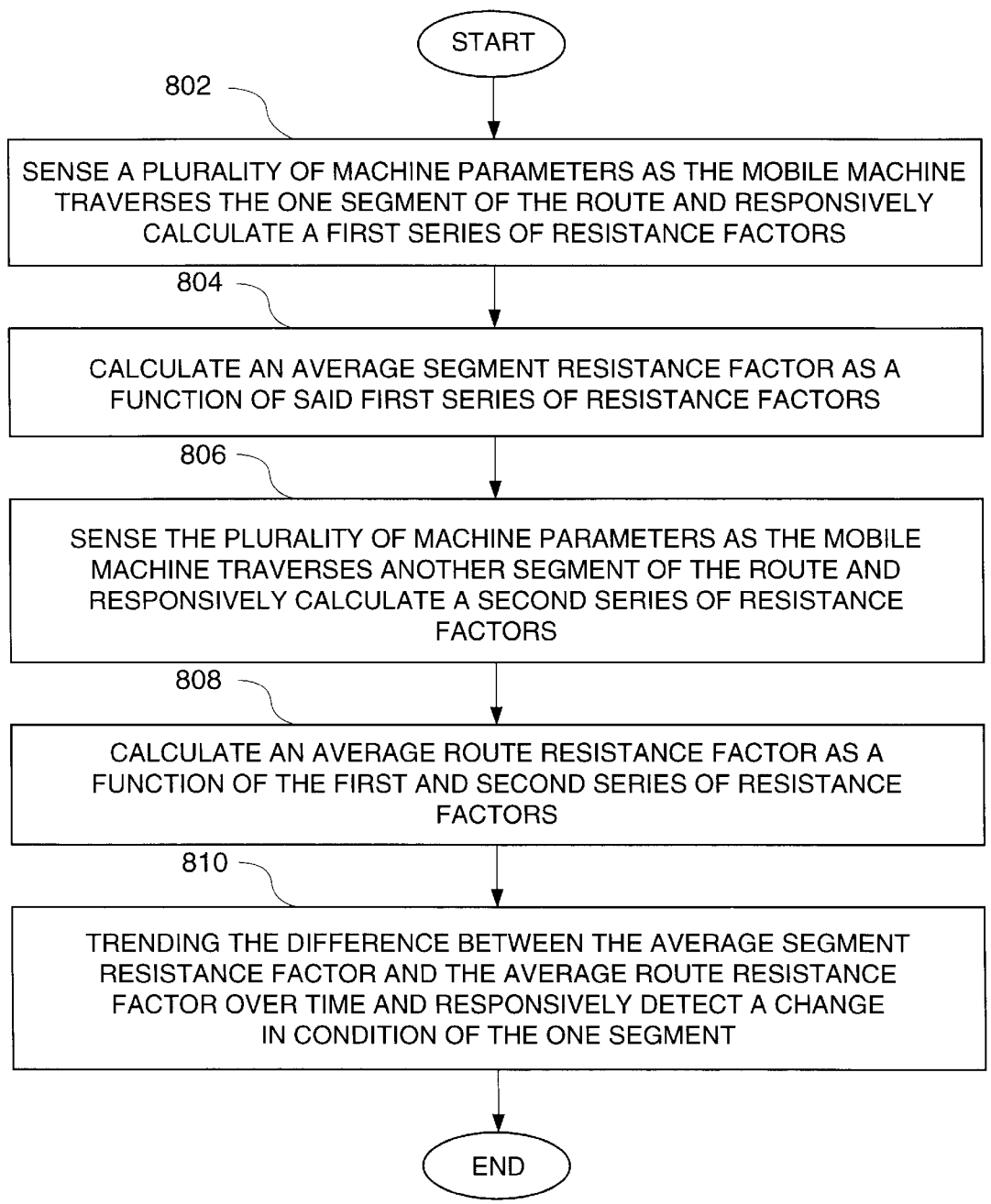

METHOD FOR DETECTING AN ABNORMAL CONDITION OF A ROAD SURFACE BY TRENDING A RESISTANCE FACTOR

This is a Continuation-in-Part of application Ser. No. 08/616,869 filed Mar. 15, 1996, now abandoned.

TECHNICAL FIELD

The present invention relates generally to an earthmoving machine, and more particularly, to a method for determining a resistance factor in order to detect an abnormal condition of a road surface.

BACKGROUND ART

Electronic control modules and information systems are becoming key components on earthmoving machines. Electronic control modules typically include a plurality of sensors and a microprocessor based control module adapted to control a machine component.

Typical electronic control modules on earthmoving machines control operation of the engine or transmission. Information systems are also used to collect data relating to the operation of the earthmoving machine and to store the data and/or display the data to the operator.

The data being collected presents a previously unknown opportunity to diagnose and/or monitor in real time the operation of the machine or environment which normally have to be accomplished manually.

The present invention is aimed at one or more of the problems identified above.

DISCLOSURE OF THE INVENTION

In one aspect of the present invention, a method for detecting a change in the condition of a road traversed by a fleet of at least one mobile machine is provided. The method includes the steps of sensing a plurality of machine parameters as the mobile machine traverses a segment of the road and responsively calculating a plurality of machine resistance factors each time the mobile machine traverses the segment. An average resistance factor is calculated as a function of the series of machine resistance factors and the average resistance factor is trended over time in order to detect a change in the road condition.

In another aspect of the present invention, a method for detecting a changed condition of one segment of a route traversed by a fleet of at least one mobile machine is provided. The route is composed of the segment and at least one other segment. The method includes the steps of sensing a plurality of machine parameters of the mobile machine as it traverses the one segment of the route and responsively calculating a first series of a resistance factors. An average resistance factor is calculated as a function of the first series of resistance factors. The plurality of machine parameters are sensed as the mobile machine traverses the one other segment of the route and a second series of resistance factors are calculated. An average route resistance factor is calculated as a function of the first and second series of resistance factors. The difference between the average resistance factor for the one segment and the average route resistance factor is trended over time and a change in condition of the one segment is detected.

BRIEF DESCRIPTION OF THE DRAWINGS

FIG. 1 is a side view graphical illustration of an earthmoving machine shown as an off-highway truck as it traverses a road segment;

FIG. 2 is a block diagram of an apparatus for implementing the present invention;

FIG. 3 is a graph illustrating an example of the resistance factor and the average resistance factor as the mobile machine travels from A to B;

FIG. 4 is a graph illustrating average resistance factors as the mobile machine travels from A to B under different conditions;

FIG. 5 is a graph illustrating the difference between the resistance factor over one segment and the resistance factor over a number of segments trended over time;

FIG. 6 is a graph illustrating the average resistance factor of a path segment trended over time;

FIG. 7 is a flow diagram illustrating a method for detecting a change in condition of a road, according to an embodiment of the present invention; and FIG. 8 is a flow diagram illustrating a method for detecting a change in condition of a road, according to an other embodiment of the present invention.

BEST MODE FOR CARRYING OUT THE INVENTION

With reference to FIG. 1, the present invention is adapted to provide a method for automatically detecting an abnormal condition of a road 104 as a mobile machine 102 or fleet of like machines travel along a path on the road.

In the preferred embodiment, the mobile machine 102 is shown as an off-highway truck. However, other similar machines may be used without departing from the spirit of the invention.

With reference to FIG. 2, the present invention is implemented in a controlling means 202. In the preferred embodiment, the controlling means 202 includes a microprocessor based controller 204.

A sensing means 206, which includes a plurality of sensors 208, senses a plurality of parameters of the earthmoving machine 102 as it traverses the path.

A positioning means 210 determines the position of the earthmoving machine 102. The positioning means 210 includes a position sensor 212 which in the preferred embodiment includes Global Positioning System (GPS) receiver (not shown). The GPS receiver receives signals from satellites and responsively determines the position of the receiver. It should be noted, however, that other positioning sensors, for example laser based systems, may be used without departing from the spirit of the invention.

Data from the earthmoving machine 102 may be delivered to a remote location 218 or remote station 220 via a transmitting means 214. The transmitting means 214 preferably includes a transmitter 216.

As discussed below, the present invention provides a method for detecting an abnormal condition of the road surface. This is accomplished via the calculation of a resistance factor (RF) over portions or segments of the road. In the preferred embodiment, the resistance factor is normalized.

The resistance factor can be either a total resistance factor (TRF) or a rolling resistance factor (RRF).

The total resistance factor has two components: the rolling resistance factor and SLOPE. The rolling resistance factor is attributed to the force applied to the mobile machine 102 by the road surface and the SLOPE of the grade is the component vector of gross vehicle weight (GVW) acting parallel to the road surface, i.e., slope component is grade resistance=$\sin(\theta) \times GVW$.

As described below, the resistance factor can be either TRF or RRF.

With reference to FIG. 3 in the top portion of the graph, a sample resistance factor (RF) is illustrated for a path segment from A to B. As shown, the path segment from A to B is composed of a series of smaller sub-segments (A-a1, a1-a2,a2-a3,a3-B). Line segment 302 represents a series of resistance factors calculated as the machine traverses from point A to point B.

In the lower portion of the graph, an average resistance factor for each subsegment is shown. The line segment 304 represents the average resistance factor for each subsegment.

With reference to FIG. 4, the graph illustrates an average resistance factor for each subsegment under different conditions. Solid line 402 represents the average resistance factor under normal operating conditions. Dotted line 404 represents the average resistance factor over each subsegment as the condition of each subsegment deteriorates. Dotted line 406 represents the average fleet resistance factor over each subsegment where the condition of the road for segment A-a$_1$ has deteriorated a greater amount than the other subsegments.

The average resistance factor for each subsegment is calculated as the average of the average resistance factors determined as each machine in the fleet traverses the sub-segment.

The resistance factors are calculated by the following procedure:

First, the weight of the fuel in the fuel tank of the mobile machine 102 is determined according to Equation 1:

$$FW = FG/100 \times FC \times FD \times g \qquad \text{Equation 1}$$

where FW represents the fuel weight, FG represents the signal received from a fuel gauge, FC represents the fuel capacity of the mobile machine 102, FD represents the fuel density of the fuel being used, and g represents the gravitational constant. FC, FD, and g are constants.

The gross vehicle weight (GVW) is then determined by:

$$GVW = EVW + FW + PW \qquad \text{Equation 2}$$

where EVW represents the empty vehicle weigh and PW represents the weight of the payload being carried by the mobile machine 102. EVW is a constant and PW determined by a sensor.

The net rimpull is determined by the equation:

$$NRP = DLRP - BRKP \qquad \text{Equation 3}$$

where DLRP represents the drivetrain rimpull and BRKP represents the braking power. Drivetrain rimpull and braking power may be determined directly by sensors or may be determined by computer based models using other sensor information.

The wind resistance is determined by the equation:

$$WR = CD \cdot (VSPD)^2 \qquad \text{Equation 4}$$

where VSPD represents the speed of the machine and is determined by a sensor and CD represents the coefficient of drag of the mobile machine and is a constant.

The acceleration of the mobile machine (VACC) is determined as the time derivative of the machine speed.

The total resistance factor (TRF) is then determined by the equation:

$$TRF = \frac{NRP - WR}{GVW} - \frac{VACC}{g} \qquad \text{Equation 5}$$

As stated previously, the resistance factor is either a rolling resistance factor or a total resistance factor and a slope component.

In order to determine the rolling resistance factor, the slope component must be subtracted from the total resistance factor. The slope component is equal to the sine of the angle of the path segment. The slope angle may be predetermined and constant or calculated based on the end position and the start position of the segment or sub-segment as determined by the positioning means 210.

The rolling resistance factor is calculated by the equation:

$$RF = TRF - \text{SLOPE} = \frac{NRP - WR}{GVW} - \frac{VACC}{g} - \text{SINE}(\theta) \qquad \text{Equation 6}$$

where $\theta$ is the slope angle of the path relative to horizontal.

With reference to FIG. 7, the present invention is adapted to detect a degradation in the road condition of a single path segment, for example, A-a1.

In a first control block 702, a plurality of machine parameters is sensed as the mobile machine traverses a segment of the road (A-a1) and a plurality or series of machine resistance factors are calculated each time the mobile machine traverses the segment.

In a second control block, an average resistance factor is calculated as a function of the series of machine resistance factors. An average resistance factor is calculated each time a machine in the fleet traverses the path segment or sub-segment.

In a third control block 706, the average resistance factor is trended over time and a change in condition of the road is detected.

As conditions in the road segment deteriorate, for example, during wet conditions, the resistance factor will increase. With reference to FIG. 6, an exemplar graph of the resistance factor over subsegment A-a1 is illustrated.

In one embodiment, the trending of the third control block 706 is accomplished by comparing the resistance factor with a predetermined threshold. If the resistance factor exceeds the threshold, then a change in the condition of the road is said to have occurred.

In another embodiment, the trending of the third control block 706 is accomplished by comparing a rate of change of the resistance factor with a predetermined threshold. If the rate of change in the resistance factor exceeds the threshold, then a change in the condition of the road is said to have occurred.

In still another embodiment, the trending of the third control block 706 is accomplished by determining a rate of change in the resistance factor and estimating a time at which the resistance factor will exceed or equal a predetermined threshold. If the time is less than a second predetermined threshold, then a change in the condition of the road is said to have occurred.

It should be noted that other types of trending may be used without departing from the spirit of the invention.

It should be noted that path segment A-B, may be treated as a single path segment for purposes of detecting degradation in the path segment. In other words, a single average resistance factor may be calculated over the path segment A-B and trended to detect the degradation in the road surface from A to B.

Additionally, an average resistance factor may be determined for a series of discontiguous path segments and an average resistance factor for all path segments in the series may be calculated. The average resistance factor for the discontiguous path segments may be trended to determine a degradation in the road surface for all path segments.

In another embodiment of the present invention, a degradation in a path segment with respect to other path segments is be detected.

With particular reference to FIG. 8, in the another embodiment, an average resistance factor is calculated for a plurality of subsegments as each machine in the fleet traverses the subsegments.

In a fourth control block 802, a plurality of machine parameters is sensed as the mobile machine traverses the one segment of the route and a first series of resistance factors is calculated.

In a fifth control block 804, an average segment resistance factor is calculated as a function of the first series of resistance factors. An average segment resistance factor is calculated each time one machine in the fleet traverses the one segment.

In a sixth control block, the plurality of machine parameters are sensed as the mobile machine traverses another segment in the route and a second series of resistance factors is calculated.

In a seventh control block 808, an average route resistance factor is calculated as a function of the first and second series of resistance factors.

In the preferred embodiment, the route is composed of the one segment and at least one other segment. If there are more than two segments, a series of resistance factors for each segment is determined. The average route resistance factor is determined as a function of all series of resistance factors. The segments comprising the route may be contiguous or noncontiguous.

Additionally, an average resistance factor for each segment may be determined and trended against the average route resistance factor.

In an eighth control block 810, the difference between the average segment resistance factor and the average route resistance factor is trended over time. A change in condition of the one segment is detected based on the trending.

With particular reference to FIG. 5, as shown, the resistance factor of the one segment ($RF_{(A-a1)}$) and the resistance factor from A to B ($RF_{(A-B)}$) is trended.

In one embodiment, the trending of the eighth control block 810 is accomplished by comparing the difference between the average segment resistance factor and the average route resistance factor, as illustrated by line 502, with the predetermined threshold. If the difference exceeds the threshold, then a change in the condition of the one segment (A-a1) is said to have occurred. This is indicative of a change in condition of the one segment relative to the other segments.

As described previously, other types of trending may be used without departing from the spirit of the invention.

INDUSTRIAL APPLICABILITY

With reference to the drawings and in operation, the present invention is adapted to provide a method for automatically and in real time detect an abnormal condition in a road surface.

As the earthmoving machine 102 travels along a segment of a path on the road, a plurality of parameters of the earthmoving machine are sensed. The parameters are used to calculate a resistance factor for the path segment. The calculated resistance factor is compared with an average resistance factor and an abnormal condition of the road surface is responsively detected.

Operation of the present invention may be invisible to the operator. Data is sensed and determined during operation and the abnormal condition is detected (when present). The data may be stored onboard and/or displayed to the operator. Additionally, the data may also be transported off board via a communication link or transported manually for detection of the abnormal condition.

Other aspects, objects, and features of the present invention can be obtained from a study of the drawings, the disclosure, and the appended claims.

I claim:

1. A method for detecting a change in the condition of a road traversed by a fleet of at least one mobile machine, comprising:

sensing a plurality of machine parameters as the at least one mobile machine traverses a segment of the road and responsively calculating a plurality of machine resistance factors each time the at least one mobile machine traverses said segment;

calculating an average resistance factor as a function of said plurality of machine resistance factors; and, trending said average resistance factor over time and responsively detecting a change in condition of the road.

2. A method, as set forth in claim 1, wherein the average resistance factor is normalized.

3. A method, as set forth in claim 2, wherein the normalized resistance factor is compared with a predetermined threshold and the change in the condition is detected if the resistance factor exceeds said predetermined threshold.

4. A method, as set forth in claims 1, wherein said machine resistance factors are rolling resistance factors.

5. A method, as set forth in claim 1, wherein said machine resistance factors are total resistance factors.

6. A method for detecting a change in condition of one segment of a route traversed by a fleet of at least one mobile machine, the route composed of the one segment and at least one other segment, comprising:

sensing a plurality of machine parameters as the at least one mobile machine traverses the one segment of the route and responsively calculating a first series of resistance factors;

calculating an average segment resistance factor as a function of said first series of resistance factors;

sensing said plurality of machine parameters as the at least one mobile machine traverses the one other segment of the route and responsively calculating a second series of resistance factors;

calculating an average route resistance factor as a function of the first and second series of resistance factors; and, trending the difference between said average segment resistance factor and said average route resistance factor over time and responsively detecting a change in condition of the one segment.

7. A method, as set forth in claim 6, wherein the difference between said average segment resistance factor and said average route resistance factor is compared with a predetermined threshold and the change in the condition is detected if the difference exceeds said predetermined threshold.

8. A method, as set forth in claim 6, wherein said first and second series of machine resistance factors are rolling resistance factors.

9. A method, as set forth in claim 6, wherein said first and second series of machine resistance factors are total resistance factors.

10. A method for detecting a change in the condition of a road traversed by a fleet of at least one mobile machine, comprising:

sensing a plurality of machine parameters as said one mobile machine traverses a segment of the road, determining the force applied to said one mobile machine by the road surface, and responsively calculating a plurality of machine resistance factors each time said one mobile machine traverses said segment;

calculating an average resistance factor as a function of said plurality of machine resistance factors; and, trending said average resistance factor over time and responsively detecting a change in condition of the road.

11. A method for detecting a change in condition of one segment of a route along a road traversed by a fleet of at least one mobile machine, the route composed of the one segment and at least one other segment, comprising:

sensing a plurality of machine parameters as said one mobile machine traverses the one segment of the route, determining the force applied to said one mobile machine by the road surface, and responsively calculating a first series of resistance factors;

calculating an average segment resistance factor as a function of said first series of resistance factors;

sensing said plurality of machine parameters as said one mobile machine traverses the one other segment of the route and responsively calculating a second series of resistance factors;

calculating an average route resistance factor as a function of the first and second series of resistance factors; and, trending the difference between said average segment resistance factor and said average route resistance factor over time and responsively detecting a change in condition of the one segment.

* * * * *